(12) United States Patent
Domingo Pedrol

(10) Patent No.: US 9,271,954 B2
(45) Date of Patent: Mar. 1, 2016

(54) USE OF DOCOSAHEXAENOIC GLYCERIDES FOR THE TREATMENT OF TUMOROUS DISEASES

(75) Inventor: Joan Carles Domingo Pedrol, Barcelona (ES)

(73) Assignee: BRUDY TECHNOLOGY, S.L., Barcelona (ES)

( * ) Notice: Subject to any disclaimer, the term of this patent is extended or adjusted under 35 U.S.C. 154(b) by 0 days.

(21) Appl. No.: 12/550,780

(22) Filed: Aug. 31, 2009

(65) Prior Publication Data

US 2009/0318553 A1 Dec. 24, 2009

Related U.S. Application Data

(63) Continuation of application No. 11/913,994, filed as application No. PCT/EP2006/061844 on Apr. 26, 2006, now abandoned.

(30) Foreign Application Priority Data

May 12, 2005 (ES) .................................. 200501141

(51) Int. Cl.
*A61K 31/232* (2006.01)
*A61K 45/06* (2006.01)

(52) U.S. Cl.
CPC .............. *A61K 31/232* (2013.01); *A61K 45/06* (2013.01)

(58) Field of Classification Search
None
See application file for complete search history.

(56) References Cited

FOREIGN PATENT DOCUMENTS

| DE | 3721137 | * | 1/1989 |
| JP | 05-331105 | * | 12/1993 |
| JP | 06016548 | * | 12/1994 |
| JP | 08-60181 | * | 3/1996 |

OTHER PUBLICATIONS

Braden et al., Lipids 21:285-288, 1986.*
Reddy et al., Cancer Res. 46:3367-3370, 1986.*
Hamazaki et al., Lipids (1987), 22(12), 1031-4.*
Stillwell et al., Lipids (1993), 28(2), 103-8.*
Database CAPLUS Chemical Abstracts Service, Columbus, Ohio, US; Database Accession No. 2004:1003660, Abstract of Maeda et al., Journal of Traditional Medicines (2004), 21(5), 215-220.*
Database CAPLUS Chemical Abstracts Service, Columbus, Ohio, US; Database Accession No. 1990:204676, Abstract of DE 3721137, (1989) Dietl.*
Machine Translation of 05-331105.*
Machine Translation of 08-60181.*

* cited by examiner

*Primary Examiner* — Karl J Puttlitz
(74) *Attorney, Agent, or Firm* — Cozen O'Connor

(57) ABSTRACT

The present invention relates to the use of an oil enriched in docosahexaenoic acid, which is conjugated to triglyceride, for manufacturing a pharmaceutical composition for the treatment of a tumorous disease, said oil being enriched in a concentration of up to 70% by weight in relation to the total weight of said pharmaceutical composition, and said docosahexaenoic acid being in a percentage of at least 50% in relation to the total fatty acids in said oil.

8 Claims, No Drawings

USE OF DOCOSAHEXAENOIC GLYCERIDES FOR THE TREATMENT OF TUMOROUS DISEASES

FIELD OF THE INVENTION

The present invention relates to use of an acid enriched in docosahexaenoic acid for manufacturing a drug for the treatment of a tumorous disease.

BACKGROUND

Various evidence from studies on animals and in vitro studies indicate that the omega-3 fatty acids, and especially the long-chain polyunsaturated fatty acids (PUFAs) such as eicosapentaenoic acid (EPA) and docosahexaenoic acid (DHA), present in fish and in oils derived therefrom inhibit carcinogenesis and show potential anti-tumour activity. In vitro studies with human tumorous lines have shown convincingly that the omega-3 PUFAs, principally DHA, reduce the growth of various types of tumorous cells, including breast, bowel, pancreas, and in chronic myeloid leukaemia and melanoma. Epidemiological data on the association between fish consumption, as a marker for the take-up of omega-3 fatty acids, and the risk of cancer are nevertheless rather less consistent. It has only proved possible to establish that the ingestion of DHA and EPA reduces the growth of tumours in rodents, including tumours of the mammary gland, the colon, the prostate, the liver and the pancreas.

Moreover, various studies have shown that the omega-3 PUFAs selectively inhibit the proliferation of tumorous cells, being less toxic towards normal cells. This different sensitivity to the omega-3 PUFAs cannot be explained simply by differences in the take-up of fatty acids. Various mechanisms have been proposed by which the omega-3 fatty acids might alter the carcinogenic process, notably the following: suppression of biosynthesis of eicosanoids deriving from arachidonic acid (ARA); alterations in the activity of transcription factors, regulation of gene expression and intracellular marking; alteration of oestrogen metabolism; alteration of the generation of free radicals and reactive oxygen species and modifications in membrane fluidity.

The ARA-derived eicosanoids have been associated with tumour development. Various mechanisms exist by which the omega-3 fatty acids can reduce the biosynthesis of ARA-derived eicosanoids. Firstly, the omega-3 fatty acids are taken into the phospholipids of the membrane, where they partially replace the omega-6 fatty acids. Secondly, the omega-3 PUFAs compete with the omega-6 PUFAs as substrates of the desaturases and elongases, the omega-3 PUFAs having greater affinity for said enzymes. Finally, the omega-3 fatty acids inhibit cycloxygenase-2 at transcriptional level and compete with the omega-6 fatty acids as substrates of the cycloxygenases in formation of the eicosanoids.

Furthermore, the omega-3 PUFAs and their metabolites can exercise some of their anti-tumour effects by affecting the expression of various genes or the activities of the signal-transmission molecules involved in controlling growth, differentiation, cellular apoptosis, angiogenesis and metastasis. The most important are the activated receptor of peroxysomal proliferation, that of nuclear transcription factor KB, the ras oncogene, protein kinase C, co-enzyme-A-3-hydroxyl-3-methylglutaril reductase, cycloxygenase-2, lipoxygenases and the nitric oxide synthase. It has been shown that the treatment of colon carcinoma cells with DHA alters the characteristics of the cellular membrane and reduce its metastasic capacity.

The generation of free radicals and reactive oxygen species appears to be involved in the initiation of apoptosis and in natural defences against the transformed cells. Thus the inhibitory effects of the long-chain omega-3 PUFAs on the growth of tumour cells can be explained, at least partly, by the formation of oxidation products, which leads to growth of the cell being halted and to the onset of the apoptosis process. It has been suggested that the tumour cells have a deficit of anti-oxidant defence systems in comparison with the healthy cells and are thus more susceptible to oxidation damage. The PUFAs are the main intracellular substrates in lipid peroxidation, whether it be by causing damage to the cell membranes, altering cellular composition or the assembly of the cytoskeleton, altering the membrane transport systems or the activity of their enzymes, or inhibiting the reactions of the polymerase. It is therefore reasonable to consider the DHA-enriched cells of the tumour as being more susceptible to oxidative damage.

There is a certain amount of evidence that the omega-3 fatty acids have an effect on the cell cycle. In vitro treatment with DHA leads to a stoppage in the $G_1/S$ or $G_2/M$ phase during the cell cycle in tumorous cells of breast and melanoma. In vivo, the administration of fish oil rich in omega-3 to rats implanted with a breast tumorous line can prolong replication of the DNA of the tumorous cells thereby delaying progression through the synthesis phase.

Preclinical studies have nevertheless shown that the omega-3 PUFAs can increase the cytotoxicity of several anti-neoplasic agents and the anti-carcinogenic effects of radiotherapy. These effects are possibly mediated by incorporation of the fatty acids into the tumour cell membranes, thus altering physical and functional characteristics.

On the other hand, the therapeutic efficacy achieved depends on several factors, such as the bioavailability of the fatty acid, which is in turn related with the chemical structure of which it forms part, the type of omega-3 PUFA used (ALA, EPA or DHA) and the interaction availability between the PUFA and the target cell.

Data resulting from a study in which the bioavailability of three concentrated omega-3 PUFAs in the form of ethyl esters, free fatty acids and triglycerides were compared following oral administration showed that the re-esterified triglycerides presented greater bioavailability than the other two preparations.

It was also shown in a multi-organ model of carcinogenesis that in a monotherapy treatment DHA is the omega-3 PUFA that provides most effective anti-tumour protection, exceeding that of EPA. This result has also been confirmed in combined EPA+DHA anti-tumour treatments, where the presence of EPA has been observed to diminish the efficacy of the DHA.

Finally, the administration route is an important aspect on which the efficacy of the system depends. For example, intra-tumour administration is the preferred route for the treatment of gliomas. It is essential in this respect that the PUFAs be administered to the patients in such a way as to be easily taken up by the tumorous cells. For parenteral administration, for example, which is suitable for the treatment of hepatomas, it is essential to have a carrier system such as an emulsion with the additional objective of limiting bonding of the PUFAs to the serum albumin that suppresses their tumour cytotoxicity. In the case of oral administration, suitable for the treatment of lymphomas, following processing and intestinal absorption the PUFAs are transported to the target tissue incorporated into the kilomicrons in the form of triglycerides.

DESCRIPTION OF THE INVENTION

The present invention concerns the unexpected discovery that oils with a high content of DHA incorporated into a glyceride, in particular with a content exceeding 50% by weight, present an anti-tumour efficacy greater than the same concentration of DHA in any other chemical form.

An object of the present invention is therefore the use of an oil enriched in docosahexaenoic acid (hereinafter also referred to as "DHA") which is incorporated into a glyceride, for manufacturing a pharmaceutical composition for the treatment of a tumorous disease, with said oil being enriched by a concentration of up to 70% by weight in relation to the total weight of said pharmaceutical composition and with said docosahexaenoic acid being incorporated into a glyceride in a percentage of at least 50% by weight in relation to the total fatty acids in said oil.

In the present invention, the expression "oil enriched in docosahexaenoic acid" means natural or synthetic derivatives of glycerol containing 50-100% by weight of the docasohexaenoyl group based on the total content of fatty acids.

In the present invention, "docosahexaenoic acid incorporated into a glyceride" is taken to mean a glycerol with the three positions esterified with docosahexaenoic acid.

In the present invention, the expression "up to 70% by weight of said enriched oil" means that 70% of the total weight of the pharmaceutical composition corresponds to the DHA-enriched oil.

In the present invention, the expression "at least 50% in relation to the total fatty acids" means that the DHA represents at least 50% by weight of the total fatty acids of said enriched oil.

Surprisingly, the inventors of the present invention have found that using an amount of at least 50% of DHA doubles or even quintuples the anti-tumour effect of said DHA, thereby achieving a high specific tumourous cytotoxic activity without the existence of side-effects.

In a preferred embodiment, said pharmaceutical composition is in emulsion form.

It has been found in practice that when a pharmaceutical composition that contains an oil enriched in docosahexaenoic acid incorporated into a glyceride, as described above, is administered to a patient in emulsion form, a tumorous cytotoxic activity of the order of ten times greater is achieved (as emerges from the examples included below).

The emulsions can be prepared under apyrogenic and sterile conditions with sufficient physical and chemical stability for administration thereof, including parenteral administration, by means of methods well-known to an expert in the art.

In another preferred embodiment, the mean diameter of the microemulsion is less than 200 nm.

Advantageously, this mean diameter permits parenteral application, thereby administering an effective dose of DHA greater than that obtained by oral administration, and therefore increasing the bioavailability of said acid. This is due to avoiding the loss inherent to intestinal absorption. Furthermore, high concentrations of DHA can be administered by the parenteral route.

Due to all the foregoing, in a preferred embodiment of the present invention said pharmaceutical composition in emulsion form is administered by parenteral route. The doses to be administered depend on the type and severity of the pathology to be treated, and there are no dietary restrictions (interactions with foods).

The emulsions of the invention can also be administered orally, sublingually, intravenously, intramuscularly, topically, subcutaneously, rectally or even simply by bringing the active ingredient of the emulsion of the invention into contact with the olfactory organs situated at the entrance to the airways in liquid or vapour form. Administration can thus be carried out by spraying, nebulising or atomising the emulsions or by inhalation.

In another preferred embodiment, said pharmaceutical composition is administered by intramuscular injection.

In another preferred embodiment, said DHA-enriched oil also includes ecosapentaenoic acid (also referred to as EPA) in a percentage by weight of up to 30% in relation to the total fatty acids in said oil.

In a preferred embodiment, the concentration of DHA-enriched oil is in the range of 10-70%, preferably in the range of 10-30% in relation to the total weight of the pharmaceutical composition.

In another preferred embodiment, the percentage by weight of DHA in relation to the total weight of fatty acids of said enriched oil ranges between 50-100%, preferably between 70 and 90%, and more preferably said percentage by weight of DHA is 70%.

The inventors of the present invention have further found that when a pharmaceutical composition in accordance with the present invention is administered, there are no interactions with the components of the anti-neoplasic regime being administered to the patient, since said composition is not metabolised in pathways common to those of metabolisation of the anti-neoplasic drugs.

Therefore, in another preferred embodiment of the invention, said composition is administered concomitantly with at least one anti-neoplasic drug.

In the present invention, "anti-neoplasic drug" is taken to mean an active ingredient or drug designed for the treatment of a pathology of tumorous or cancerous origin.

Advantageously, it has been observed that joint administration of a DHA-enriched oil according to the invention together with an anti-neoplasic drug boosts the anti-tumour activity of said treatment and in turn inhibits the side-effects of the anti-tumour treatment.

There follow some examples by way of non-restrictive illustration of the present invention.

EXAMPLES

Example 1

Formulation of a Pharmaceutical Composition in Accordance with the Invention

The invention relates to a stable, non-detergent composition in microemulsion form for administration to human beings, comprising:
 between 1 and 70% by weight of a glyceride that contains DHA as the active ingredient in at least 50% of its fatty acids (Proyecto Empresarial Brudy);
 between 1 and 1.5% by weight of phospholipids of soya (Lipoid E80, Lipoid);
 2.25% by weight of glycerol (Sigma & Aldrich); and
 up to 100% of water USP (ADESCO).

The initial emulsion is homogenised repeatedly at high pressure to a suitable size and the pH is adjusted to a physiological value (between 6.5-7) with sodium hydroxide (Sigma & Aldrich). Once adjusted to the final volume, the microemulsion is sterilised by filtration (0.22 μm, Millipore) in its definitive glass receptacle.

Example 2

Evaluation of a DHA Preparation in Different Tumorous Models

This study used as an experimental tumorous model KG-1a cells (derived from an acute myeloid leukaemia which are moreover MDR+, ATCC CCL-246.1), Jurkat cells (derived from an acute type-T lymphoma, TIB-152), HeLa and KB3.1 cells (derived from a human epithelial carcinoma, CCL-2), HT-29 cells (derived from a human colon tumour, HTB-38), 435 cells (derived from a human breast tumour, MDA-MB-435), SH-SY5Y cells (derived from a human neuroblastoma, CRL-2266) and NP-18 cells (derived from a human pancreal tumour). The non-tumorous model used was Foreskin cells (non-differentiated epidermis fibroblasts, CRL-1635) and REPTC cells (renal proximal tubule cells, DPK-KTEC-H). All the cellular lines were obtained from the American Type Culture Collection, except for the NP-18 cells which were ceded by the Merck Pharm and Chemistry Bioresearch Laboratory and the REPTCs which were acquired from Dominion Pharmakine. The cell cultures were kept under suitable growth conditions: temperature (37° C.), $CO_2$ concentration (5%) and humidity (95%) in a special incubator for this purpose. The cells were kept growing in culture bottles, but were transferred to 96-well plates to allow the experiment to be carried out. Work was carried out at all times with DHA from fish oil with a variable percentage of DHA in the fatty acids composition (20, 50 or 70%) and incorporated into glycerides (TG), ethyl esters (EE) or as free fatty acid (FA).

Cell-viability studies were carried out to evaluate the cytotoxic effect of the different samples. This method consists of adding the MTT reagent (3-(4,5-dimethylthiazol-2-yl)-2,5-diphenyl-tetrazolium bromide), Sigma & Aldrich), soluble in aqueous medium, to the incubation medium. The viable cells metabolise this compound and it is converted into formazan salt. This salt is a colorimetric compound insoluble in aqueous medium, soluble in DMSO and usable as a measure of cell viability. The method consists of adding 20 µl per well of an MTT solution of 7.5 mg/ml (in excess). It is incubated for one hour at 37° C. so that the viable cells metabolise the compound and produce the formazan salt, while the non-viable cells do not metabolise. Following one hour of incubation the cells are precipitated and 100 µl of DMSO (Sigma & Aldrich) is added, which will dissolve the formazan salt. Finally, the absorbency at 550 nm is measured in a plate reader. The viability results are expressed as a percentage of optical density in relation to the controls, deeming the latter to possess 100% viability. Cell viability curves were drawn up on 96-well plates by sowing about 20,000 cells per well (following an analysis of the right number of cells in the light of their growth ratio) with an approximate volume of 200 µl of medium per well. The product-efficiency study was carried out following exposure of the cells to the product for 72 h over a sufficiently wide interval of concentrations to determine the $IC_{50}$ value, defined as the concentration of active ingredient necessary to reduce cell growth/viability to 50% in relation to control.

The experimental results were adjusted to the Hill equation using SigmaPlot 8.0 software in order to determine the $IC_{50}$, defined as the concentration of DHA necessary to reduce the viability of the culture to 50% in relation to control.

Results

The first aspect to be studied to determine the action of the DHA as an anti-tumour agent is the specificity of its cytotoxic activity. In this respect we studied the effect of the DHA on the cellular proliferation/viability of non-immortalised cells with a metabolism similar to that of a normal cell. The model used was little-differentiated Foreskin cells and human renal proximal tubule cells (RPTEC), and the results obtained are shown in Table 1.

As can be observed from the different structural variants of the DHA studied (triglyceride (TG), free fatty acid (FA) and ethyl ester (EE)), the triglyceride is the one that presents lower cytotoxicity in both models of normal cell. Under these same conditions, but in a tumorous model (HeLa cells), the different DHA variants show a very significant toxicity, with an $IC_{50}$ of less than 100 µM in all cases. The cytotoxic power remains of the order of TG>FA=EE with the same DHA content (70%).

It is also revealed that the cytotoxicity of the product resides in the presence of DHA, since a reduction of the proportion of said acid reduces the cytotoxic power (compare the results of TG-70, TG-50 and TG-20), with the threshold concentration necessary to obtain a therapeutic development being estimated as at least a 50% of content in DHA, although an optimum therapeutic effect is achieved with a DHA concentration of 70%.

TABLE 1

Effect of chemical structure and concentration on the toxicity of the DHA in normal and tumorous cellular lines

| COMPOSITION | | $IC_{50}$ (µM) | | |
|---|---|---|---|---|
| | | CELLULAR LINE | | |
| STRUCTURE | % DHA | Foreskin | RPTEC | HeLa |
| FA | 70 | 123.1 ± 9.0 | n.a. | 72.2 ± 5.8 |
| EE | 70 | 566.3 ± 53.9 | 72.6 ± 8.3 | 71.0 ± 9.7 |
| TG | 70 | 716.7 ± 41.9 | 392.7 ± 37.5 | 58.6 ± 8.8 |
| TG | 50 | 1956.0 ± 27.8 | 413.6 ± 25.6 | 564.0 ± 69.6 |
| TG | 20 | 2267.6 ± 27.9 | 3116.0 ± 158.2 | 1379.4 ± 286.4 |

The second aspect studied was the applicability spectrum of the DHA as an anti-tumour drug, with its chemical structure and the nature of the pathological process at which it is directed being deemed as variables, and maintaining the DHA content at 70%. The results obtained are shown in Table 2.

TABLE 2

Effect of chemical structure on the cellular toxicity of the DHA on cellular lines of different pathological origin

| CELLULAR | $IC_{50}$ (µM) | | |
|---|---|---|---|
| LINE | FA | TG | EE |
| KG-1a | 88.4 ± 8.0 | 27.1 ± 3.2 | 120.8 ± 15.1 |
| Jurkat | 61.8 ± 4.5 | 22.1 ± 1.2 | 104.6 ± 12.6 |
| HT-29 | 158.2 ± 19.6 | 115.8 ± 17.3 | n.a. |
| 435P | 193.1 ± 20.9 | 129.7 ± 14.9 | n.a. |
| NP18 | n.a. | 18.8 ± 3.0 | n.a. |
| KB3.1 | n.a. | 116.2 ± 15.7 | n.a. |
| HeLa | 72.2 ± 5.8 | 58.6 ± 8.8 | 71.0 ± 9.7 |
| SH-SY5Y | n.a. | 86.8 ± 6.8 | n.a. |

The most notable feature is the retention of the cytotoxic potency, which follows the order TG>FA>EE in all the models used, interdependently of their origin. From the results obtained we might stress, firstly, the greater sensitivity to the DHA (5-8 times greater) for tumorous processes of a haematological nature (Jurkat and KG-1a) as against the solid tumours (the rest). As an exception that confirms the rule, great sensitivity is observed in cells derived from a pancreatic tumour (NP18).

On the basis of these results it was decided to use as active ingredient a triglyceride with a proportion of DHA equal to or exceeding 70% of the total fatty acids, since this is the one that maintains an optimum relationship between tumorous cytotoxicity and innocuousness to the normal cell.

Taking account of these considerations, an emulsion was prepared as described in the preceding section, with a proportion by weight of oil of 10% and containing various proportions of DHA, and a comparative study of its cytotoxic specificity in relation to triglyceride of free DHA was conducted. The results obtained are shown in Table 3, using as control a microemulsion of oleic acid prepared under the same conditions as the DHA microemulsion.

A behaviour similar to that described for the free triglyceride was observed. The cytotoxicity of the microemulsions is very much greater in a tumorous line (HeLa cells) than in a normal one (Foreskin cells), depending directly on the concentration of DHA in the glyceride. Moreover, the toxicity observed is attributable solely to the DHA and not to the carrier system (emulsion), since an emulsion of the same characteristics prepared with an oleic acid triglyceride is entirely innocuous.

The cytotoxic efficacy of the DHA microemulsions against the different tumorous lines was also analysed, and the results obtained are shown in Table 4, using once again as control a microemulsion of oleic acid prepared under the same conditions as the DHA microemulsion.

The results obtained confirm that the emulsions of DHA are at least as effective in their anti-tumour activity as DHA incorporated into a free glyceride. For cells derived from solid tumours or cells of epithelial origin the efficacy is 1.5-3 times greater. The non-toxicity of the carrier system (emulsion) is likewise confirmed, since an emulsion of the same characteristics prepared with an oleic acid triglyceride is entirely innocuous.

TABLE 3

Effect of the content in DHA on the comparative cytotoxicity of a glyceride in free form or incorporated into a microemulsion on normal and tumorous cellular lines

| COMPOSITION | | $IC_{50}$ (μM) CELLULAR LINE | |
|---|---|---|---|
| % DHA | STRUCTURE | FORESKIN | HELA |
| 70 | TG | 716.7 ± 41.9 | 58.6 ± 8.8 |
|  | μEMULSIÓN | 639.3 ± 27.2 | 19.5 ± 2.0 |
| 50 | TG | 1956.0 ± 27.8 | 564.0 ± 69.6 |
|  | μEMULSIÓN | >5000 | 545.8 ± 68.5 |
| 20 | TG | 2267.6 ± 27.9 | 1379.4 ± 286.4 |
|  | μEMULSIÓN | >5000 | 2135.6 ± 189.3 |
| 0 (OLEIC ACID) | μEMULSIÓN | >5000 | >5000 |

TABLE 4

Study of the comparative cellular cytotoxicity of DHA incorporated into a glyceride in free form or in microemulsions on cellular lines of different pathological origin

| | $IC_{50}$ (μM) | | |
|---|---|---|---|
| CELLULAR LINE | free TG | 10% microemulsion DHA | OLEIC ACID |
| KG-1a | 27.1 ± 3.2 | 49.5 ± 2.7 | >5000 |
| Jurkat | 22.1 ± 1.2 | 37.2 ± 1.3 | >5000 |
| HT29 | 115.8 ± 17.3 | 86.9 ± 3.5 | >5000 |
| 435P | 129.7 ± 14.9 | 61.2 ± 2.5 | >5000 |
| HeLa | 58.6 ± 8.8 | 19.5 ± 2.0 | >5000 |
| NP18 | 18.8 ± 3.0 | 10.8 ± 1.9 | >5000 |

The invention claimed is:

1. A method for treating a tumor which comprises contacting said tumor with a pharmaceutical composition comprising an oil enriched in DHA triglyceride, wherein said oil comprises 20-70% by weight of a DHA glyceride; and wherein said DHA triglyceride comprises at least 50% in relation to the total fatty acids in said oil; and wherein the enriched oil comprises between 10-70% of the total weight of said pharmaceutical composition.

2. The method according to claim 1, characterized in that said pharmaceutical composition is in emulsion form.

3. The method according to claim 1, wherein said enriched oil comprises eicosapentaenoic acid in a percentage by weight of up to 30% in relation to all acyl groups of fatty acids of said oil.

4. The method according to claim 1, wherein the concentration of docosahexaenoic acid is in a percentage of 70%-90% by weight in relation to all acyl groups of fatty acids in said oil.

5. The method according to claim 4, wherein said DHA triglyceride is in a percentage of 70% by weight in relation to the total fatty acids in said oil.

6. The method according to claim 2, wherein the mean diameter of the emulsion is less than 200 nm.

7. The method according to claim 1, wherein the tumor to be treated is one of the group that includes: lung, prostate, bowel, breast, pancreas, brain, central and peripheral nervous system, melanoma.

8. The method according to claim 1 wherein the tumor to be treated is of a haematological nature.

* * * * *

UNITED STATES PATENT AND TRADEMARK OFFICE
CERTIFICATE OF CORRECTION

PATENT NO.         : 9,271,954 B2
APPLICATION NO.    : 12/550780
DATED              : March 1, 2016
INVENTOR(S)        : Joan Carles Domingo Pedrol It is certified that error appears in the above-identified patent and that said Letters Patent is hereby corrected as shown below:

In the Claims

Column 8, line 39, Claim 4, the words "docosahexaenoic acid" should read --DHA triglyceride--.

Column 8, line 51, Claim 7, after the word "system," insert the word --and--.

Signed and Sealed this
Seventh Day of June, 2016

Michelle K. Lee
*Director of the United States Patent and Trademark Office*